United States Patent
Patton et al.

(10) Patent No.: US 8,458,864 B1
(45) Date of Patent: Jun. 11, 2013

(54) MULTI-PURPOSE UTILITY STRAP DEVICE

(76) Inventors: Renata Patton, Raleigh, NC (US); John R. Gilbert, Seattle, WA (US)

(*) Notice: Subject to any disclaimer, the term of this patent is extended or adjusted under 35 U.S.C. 154(b) by 173 days.

(21) Appl. No.: 12/978,502

(22) Filed: Dec. 24, 2010

Related U.S. Application Data

(63) Continuation-in-part of application No. 29/368,196, filed on Aug. 19, 2010, now Pat. No. Des. 659,057.

(51) Int. Cl.
*A44B 18/00* (2006.01)
*B65D 63/10* (2006.01)

(52) U.S. Cl.
USPC .................. 24/306; 24/16 R; 24/442; 24/298; 24/302

(58) Field of Classification Search
None
See application file for complete search history.

(56) References Cited

U.S. PATENT DOCUMENTS

| | | | |
|---|---|---|---|
| 4,015,762 A | 4/1977 | Mendillo | |
| 4,712,646 A | 12/1987 | Page | |
| D308,465 S | 6/1990 | Hietter | |
| 4,939,818 A * | 7/1990 | Hahn | 24/16 R |
| 5,136,759 A | 8/1992 | Armour, II | |
| 5,289,619 A | 3/1994 | Pileggi | |
| D373,750 S | 9/1996 | Gunderson | |
| D375,924 S | 11/1996 | Kramer | |
| D401,137 S | 11/1998 | Boelling | |
| 6,425,634 B1 | 7/2002 | Romero | |
| D471,006 S | 3/2003 | French | |
| D506,709 S | 6/2005 | Choi | |
| D511,450 S | 11/2005 | Seth | |
| D570,256 S | 6/2008 | Tucker | |
| D623,851 S | 9/2010 | Clayton | |
| 2001/0047607 A1 | 12/2001 | Harvanek | |
| 2009/0038123 A1 | 2/2009 | Coronel | |

* cited by examiner

Primary Examiner — Jack W. Lavinder

(57) ABSTRACT

A multi-purpose utility strap featuring an elongated strap component having an identical first end and second end. A first attachment component is disposed on the top surface of the strap component at the first end, a second attachment component is disposed on the top surface of the strap component next to the first attachment component, a third attachment component is disposed on the bottom surface of the strap component at the second end, and a fourth attachment component is disposed on the top surface of the strap component a distance from the second end. The first attachment component is adapted to engage the second attachment component to form a loop, and the third attachment component is adapted to engage the fourth attachment component to form a loop.

16 Claims, 4 Drawing Sheets

MULTI-PURPOSE UTILITY STRAP DEVICE

FIELD OF THE INVENTION

The present invention is directed to an accessory strap, more particularly to a utility strap that can be used for a variety of purposes, more particularly to a utility strap having open ends that can be looped via hook-and-loop fasteners.

BACKGROUND OF THE INVENTION

Individuals with limited mobility may find it difficult to propel themselves into vehicles or keep themselves stabilized in wheelchairs. The present invention features a multi-purpose utility strap. The utility strap may be used for a variety of purposes. For example, in some embodiments, the utility strap is used (i) to help an individual get in and out of a vehicle (e.g., the utility strap can loop around a car frame); (ii) as a safety belt to help prevent patients from falling (e.g., out of a wheelchair, etc.); (iii) as a storage strap for a walker/wheelchair (e.g., ties down); (iv) to help keep patients tied down to a chair (e.g., wheelchair) or bed; (v) as a foot lift to help transport patients on walkers; and (v) other uses, for example to help strap down skis.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

In summary, the present invention features a multi-purpose utility strap that can be used for a variety of purposes. In some embodiments, the multi-purpose utility strap comprises an elongated strap component 110 having a first end 111, a second end 112, a top surface 113, and a bottom surface 114, the first end 111 and second end 112 being identical; a first attachment component 120a disposed on the top surface 113 of the strap component 110 at the first end 111 and a second attachment component 120b disposed on the top surface 113 of the strap component 110 next to or near the first attachment component 120a, the first attachment component 120a is adapted to engage the second attachment component 120b to form a temporary loop at the first end 111 of the strap component 110; and a third attachment component 120c disposed on the bottom surface 114 of the strap component 110 at the second end 112 and a fourth attachment component 120d disposed on the top surface 113 of the strap component 110 a distance from the second end 112, the third attachment component 120c is adapted to engage the fourth attachment component 120d to form a temporary loop at the second end 112 of the strap component 110.

In some embodiments, the strap component 110 is between about 20 to 30 inches in length as measured from the first end 111 to the second end 112. In some embodiments, the strap component 110 is between about 30 to 50 inches in length as measured from the first end 111 to the second end 112.

In some embodiments, the first attachment component 120a is a first half hook-and-loop fastener and the second attachment component 120b is a second half hook-and-loop fastener. In some embodiments, the first attachment component 120a is a first half snap and the second attachment component 120b is a second snap. In some embodiments, the first attachment component 120a and the second attachment component 120b comprise a hook mechanism, a button mechanism, a tie mechanism, a magnet mechanism, a snap mechanism, or a combination thereof.

In some embodiments, the third attachment component 120c and the fourth attachment component 120d are disposed on the top surface 113 of the strap component 110 along with the first attachment component 120a and the second attachment component 120b. In some embodiments, the third attachment component 120c is a first half hook-and-loop fastener and the fourth attachment component 120d is a second half hook-and-loop fastener. In some embodiments, the third attachment component 120c is a first half snap and the fourth attachment component 120d is a second snap. In some embodiments, the third attachment component 120c and the fourth attachment component 120d comprise a hook mechanism, a button mechanism, a tie mechanism, a magnet mechanism, a snap mechanism, or a combination thereof.

In some embodiments, the first attachment component 120a can engage the fourth attachment component 120d. In some embodiments, the third attachment component 120c can engage the second attachment component 120b. In some embodiments, the third attachment component 120c can engage the first attachment component 120a. In some embodiments, the fourth attachment component 120d can engage the second attachment component 120b.

DESCRIPTION OF PREFERRED EMBODIMENTS

Figure 1:
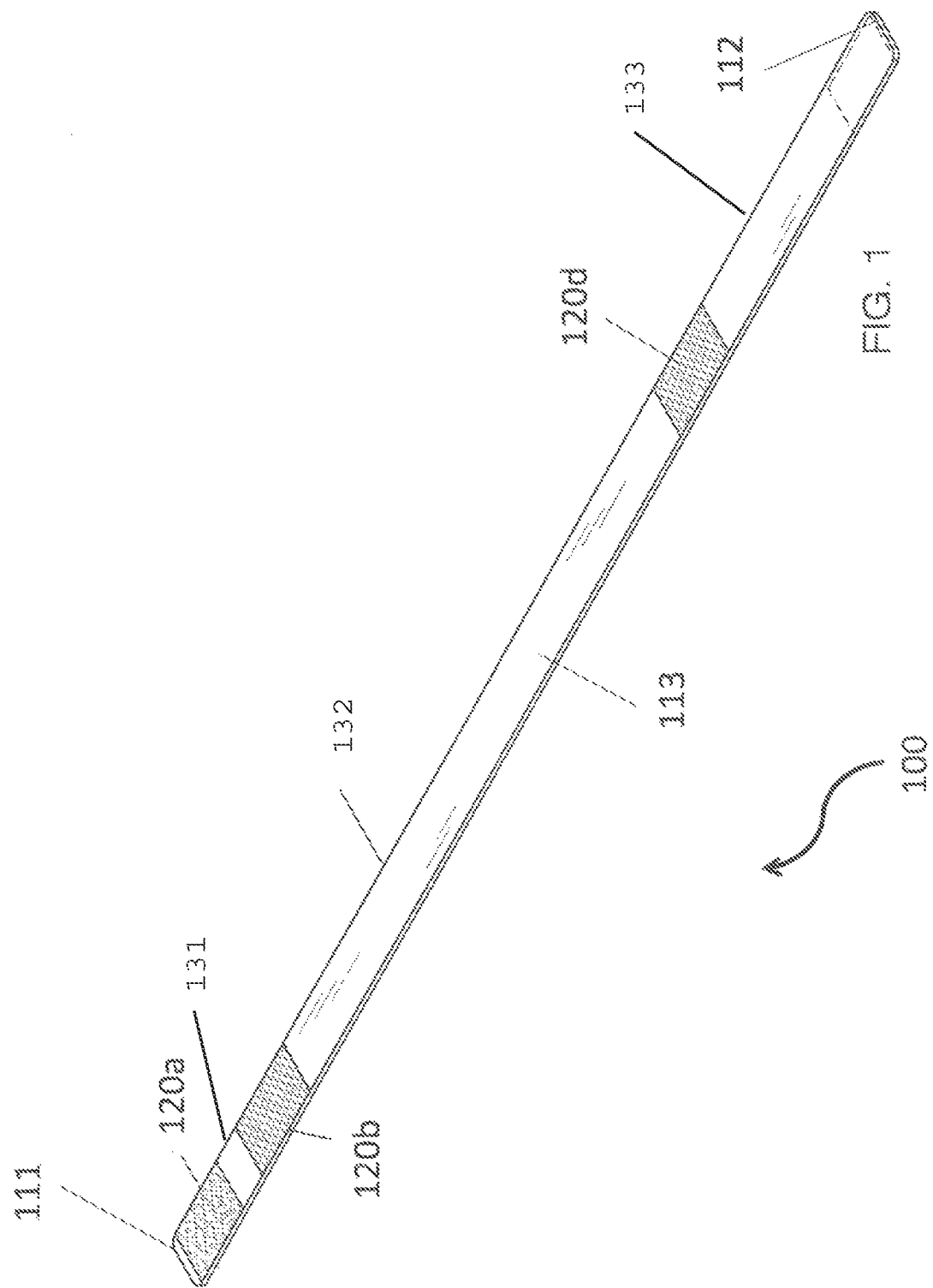
FIG. 1 is a top perspective view of the utility strap of the present invention.
Figure 2:
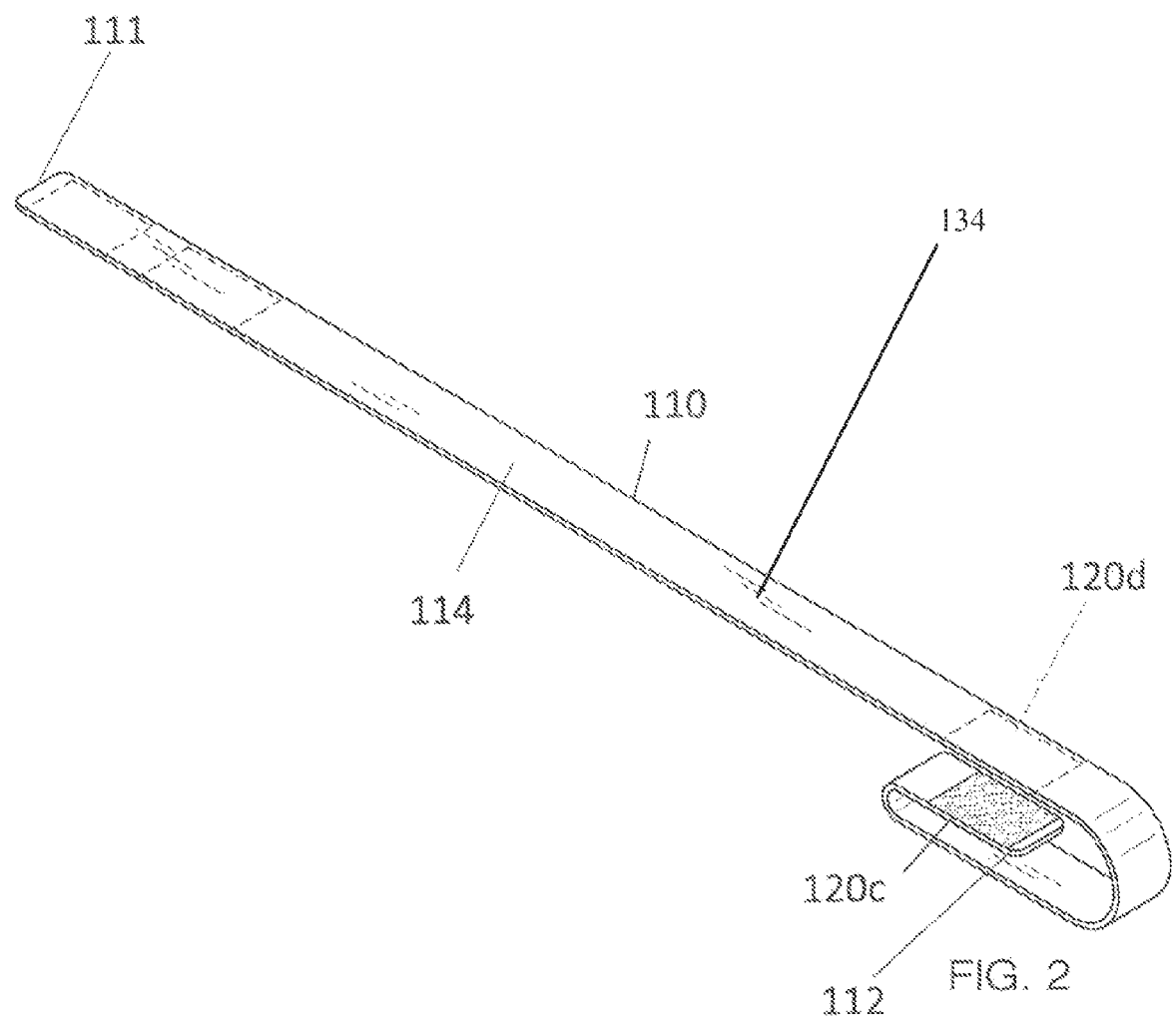
FIG. 2 is a bottom perspective view of the utility strap of the present invention.
Figure 3:
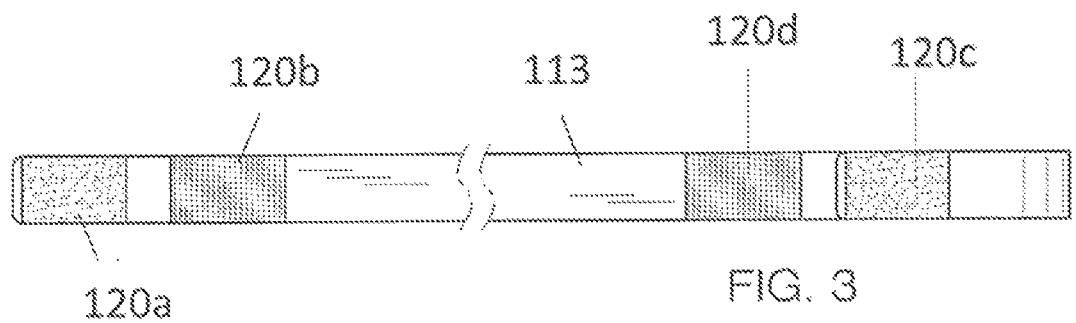
FIG. 3 is a front view of the utility strap of the present invention.

Referring now to FIG. 1-5, the present invention features a multi-purpose utility strap 100. The utility strap 100 may be used for a variety of purposes. For example, in some embodiments, the utility strap 100 is used (i) to help an individual get in and out of a vehicle (e.g., the utility strap 100 can loop around a car frame); (ii) as a safety belt to help prevent patients from falling (e.g., out of a wheelchair, etc.); (iii) as a storage strap for a walker/wheelchair (e.g., ties down); (iv) to help keep patients tied down to a chair (e.g., wheelchair) or bed; (v) as a foot lift to help transport patients on walkers; and (v) other uses, for example to help strap down skis.

Without wishing to limit the present invention to any theory or mechanism, it is believed that the device 100 of the present invention is advantageous because both ends are the same. Also, the device 100 is one size fits all. In some embodiments, the device 100 has a length of about 45 inches so as to fit average to extra large walkers. The device 100 can be used for multiple purposes including for preventing the walker from opening (when stored). The device can be used on new or existing walkers or wheelchairs.

The utility strap 100 comprises a generally elongated strap component 110 having a first end 111, a second end 112, a top surface 113, and a bottom surface 114. The strap component 110 may be constructed in a variety of sizes and from a variety of materials. For example, in some embodiments, the strap component 110 is between about 20 to 25 inches in length as measured from the first end 111 to the second end 112. In some embodiments, the strap component 110 is between about 25 to 30 inches in length as measured from the first end 111 to the second end 112. In some embodiments, the strap component 110 is between about 30 to 35 inches in length as measured from the first end 111 to the second end 112. In some embodiments, the strap component 110 is between about 35 to 40 inches in length as measured from the first end 111 to the second end 112. In some embodiments, the strap component 110 is between about 40 to 45 inches in length as measured from the first end 111 to the second end 112. In some embodiments, the strap component 110 is between about 45 to 50 inches in length as measured from the first end 111 to the second end 112. In some embodiments, the strap component 110 is between about 50 to 55 inches in length as measured from the first end 111 to the second end 112. In some embodiments, the strap component 110 is more than about 55 inches in length. In some embodiments, the strap component 110 is adjustable in length. In some embodiments, the strap component 110 or portions thereof are generally flexible or rigid.

Disposed on the top surface 113 of the strap component 110 at the first end 111 is a first attachment component 120a. In some embodiments, a second attachment component 120b is disposed on the top surface of the strap component 110 near but not touching the first attachment component 120a. A first non-attaching region 131 disposed on the top surface 113 is the part of the strap at the first end 111 between the first attachment component 120a and the second attachment component 120b; the first non-attaching region 131 has only a strap component and no attachment components. The first attachment component 120a is adapted to engage the second attachment component 120b, for example to form a temporary loop at the first end 111 of the strap component 110. For example, in some embodiments, the first attachment component 120a is a first half hook-and-loop fastener and the second attachment component 120b is a second half hook-and-loop fastener. Or, in some embodiments, in some embodiments, the first attachment component 120a is a first half snap or fastener and the second attachment component 120b is a second snap or fastener. In some embodiments, the first attachment component 120a and the second attachment component 120b comprise a hook mechanism, a button mechanism, a tie mechanism, a magnet mechanism, a snap mechanism, the like, or a combination thereof. The first attachment component 120a and the second attachment component 120b are not limited to the aforementioned attachment mechanisms.

Disposed on the bottom surface 114 of the strap component 110 at the second end 112 is a third attachment component 120c. In some embodiments, a fourth attachment component 120d is disposed on the top surface 113 of the strap component 110 a distance from the second end 112 (see FIG. 1). The part of the strap between the second attachment component 120b and the fourth attachment component 120d is a second non-attaching region 132, which is disposed on the top surface 113, and the length of second non-attaching region 132 is longer than the length of first non-attaching region 131. The part the strap between the fourth attachment component 120d and the third attachment component 120c is a third non-attaching region 133 at the second end 112, and the length of second non-attaching region 132 is longer than the length of third non-attaching region 133. The third non-attaching region 133 is disposed on the top surface 113. Both the second non-attaching region 132 and the third non-attaching region 133 have only a strap component and no attachment components. In some embodiments, the third attachment component 120c and the fourth attachment component 120d may be disposed on the same surface (e.g., top surface or bottom surface) of the strap component 110 as the first attachment component 120a and the second attachment component 120b. In some embodiments, the strap further comprises a fourth non-attaching region 134 disposed on the bottom surface 114 adjacent to the third attachment component 120c, and a length of the fourth non-attaching region 134 is longer than the length of the second non-attaching region 132; and the fourth non-attaching region has only a strap component and no attachment component.

The third attachment component 120c is adapted to engage the fourth attachment component 120d, for example to form a temporary loop at the second end 112 of the strap component 110. For example, in some embodiments, the third attachment component 120c is a first half hook-and-loop fastener and the fourth attachment component 120d is a second half hook-and-loop fastener. Or, in some embodiments, in some embodiments, the third attachment component 120c is a first half snap or fastener and the fourth attachment component 120d is a second snap or fastener. In some embodiments, the third attachment component 120c and the fourth attachment component 120d comprise a hook mechanism, a button mechanism, a tie mechanism, a magnet mechanism, a snap mechanism, the like, or a combination thereof. The third attachment component 120c and the fourth attachment component 120d are not limited to the aforementioned attachment mechanisms.

In some embodiments, the first attachment component 120a can engage the fourth attachment component 120d. In some embodiments, the third attachment component 120c can engage the second attachment component 120b. In some embodiments, the third attachment component 120c can engage the first attachment component 120a. In some embodiments, the fourth attachment component 120d can engage the second attachment component 120b.

Figure 4:
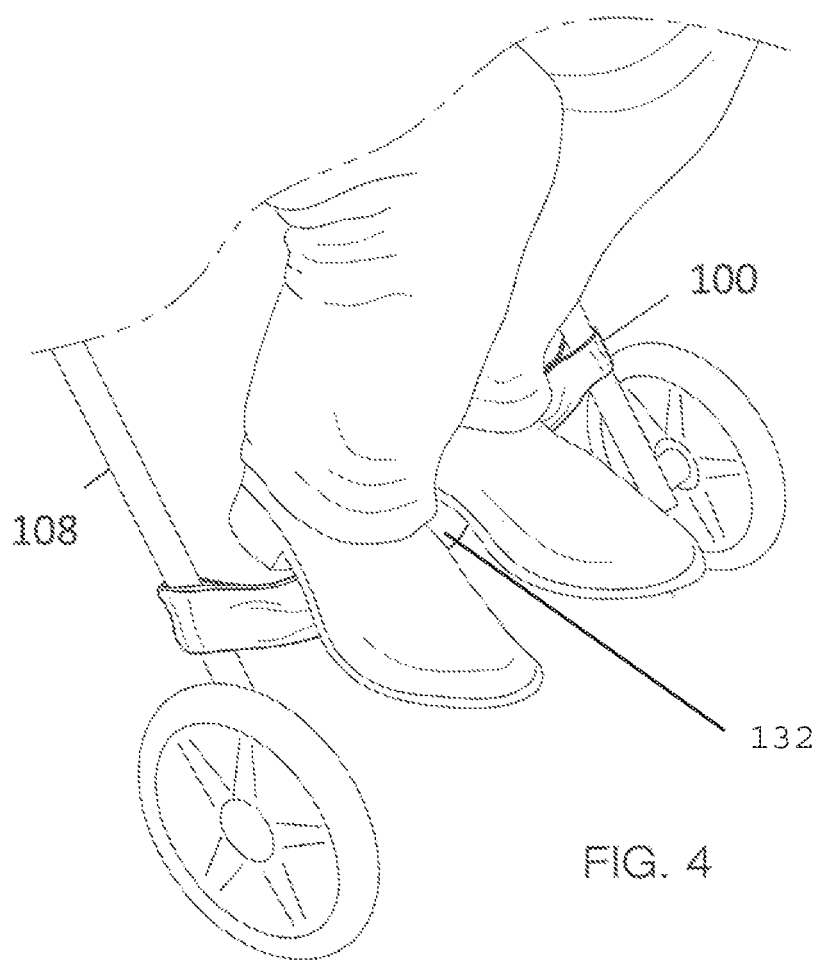
FIG. 4 is an in-use view of the utility strap of the present invention, wherein the utility strap is used on a wheelchair.
Figure 5:
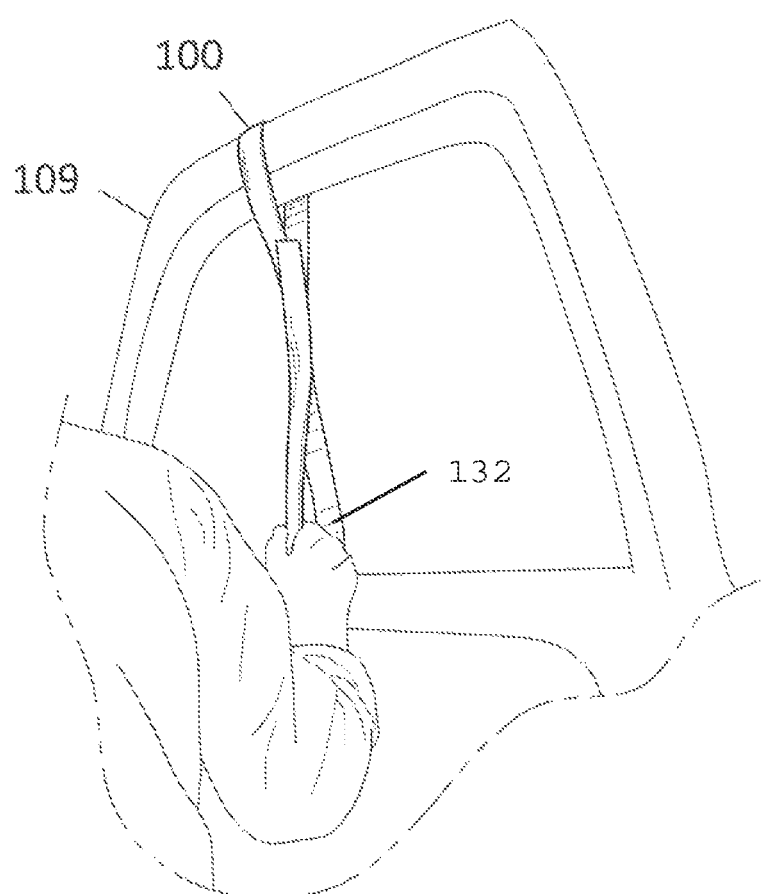
FIG. 5 is an in-use view of the utility strap of the present invention, wherein the utility strap is used to grip onto a car door.

As shown in FIG. 4, the multi-purpose utility strap 100 of the present invention is secured to the bottom frame area of a wheelchair 108 (e.g., next to a first front wheel and a second front wheel). The strap 100 provides support for a user's feet. As shown in FIG. 5, the multi-purpose utility strap 100 of the present invention is looped around a car door frame 109 to help a user propel himself/herself into a vehicle.

As used herein, the term "about" refers to plus or minus 10% of the referenced number. For example, an embodiment wherein the strap component 110 is about 20 inches in length includes a strap component 110 that is between 18 and 22 inches in length.

The disclosures of the following U.S. Patents are incorporated in their entirety by reference herein: U.S. Pat. Application No. 2001/0047607; U.S. Pat. Application No. 2009/0038123; U.S. Pat. No. 4,712,646; U.S. Pat. No. 6,425,634; U.S. Pat. No. 5,289,619; U.S. Design Pat. No. D308,465; U.S. Pat. No. 5,136,759; U.S. Design Pat. No. D401,137; U.S. Design Pat. No. D511,450.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A multi-purpose utility strap comprising:
   (a) an elongated strap component (110) having a first end (111), a second end (112), a top surface (113), and a bottom surface (114);
   (b) a first attachment component (120a) disposed on the top surface (113) of the strap component (110) at the first end (111) and a second attachment component (120b) disposed on the top surface (113) of the strap component (110) near the first attachment component (120a), the first attachment component (120a) is adapted to engage the second attachment component (120b) to form a temporary loop at the first end (111) of the strap component (110); and
   (c) a third attachment component (120c) disposed on the bottom surface (114) of the strap component (110) at the second end (112) and a fourth attachment component (120d) disposed on the top surface (113) of the strap component (110) a distance from the second end (112), the third attachment component (120c) is adapted to engage the fourth attachment component (120d) to form a temporary loop at the second end (112) of the strap component (110); and
   (d) a first non-attaching region (131) disposed on the top surface (113) of the strap at the first end (111) between the first attachment component (120a) that is on the top surface (113) and the second attachment component (120b) that is on the top surface (113), a second non-attaching region (132) disposed on the top surface (113) of the strap between the second attachment component (120b) that is on the top surface (113) and the fourth attachment component (120d) that is on the top surface (113), and a third non-attaching region (133) disposed on the top surface (113) of the strap between the fourth attachment component (120d) that is on the top surface (113) and the third attachment component (120c) that is on the bottom surface (114) at the second end (112); wherein the first non-attaching region (131), the second non-attaching region (132), and the third non-attaching region (133) have only a strap component and no attachment components; wherein a length of the second non-attaching region (132) is longer than either a length of the first non-attaching region (131) or a length of the third non-attaching region (133), and wherein the length of the third non-attaching region is longer than the length of the first non-attaching region; and
   wherein the strap further comprises a fourth non-attaching region (134) disposed on the bottom surface (114) and is adjacent to the third attachment component (120c), and a length of the fourth non-attaching region (134) is longer than the length of the second non-attaching region (132); the fourth non-attaching region has only a strap component and no attachment component.

2. The multi-purpose utility strap of claim 1, wherein the strap component (110) is between about 20 to 30 inches in length as measured from the first end (111) to the second end (112).

3. The multi-purpose utility strap of claim 1, wherein the strap component (110) is between about 30 to 50 inches in length as measured from the first end (111) to the second end (112).

4. The multi-purpose utility strap of claim 1, wherein the first attachment component (120a) is a first half hook-and-loop fastener and the second attachment component (120b) is a second half hook-and-loop fastener.

5. The multi-purpose utility strap of claim 1, wherein the first attachment component (120a) is a first half snap and the second attachment component (120b) is a second snap.

6. The multi-purpose utility strap of claim 1, wherein the first attachment component (120a) and the second attachment component (120b) comprise a hook mechanism, a button mechanism, a tie mechanism, a magnet mechanism, a snap mechanism, or a combination thereof.

7. The multi-purpose utility strap of claim 1, wherein the third attachment component (120c) is disposed on the bottom surface (114) of the strap component (110), and the fourth attachment component (120d) is disposed on the top surface (113) of the strap component (110) along with the first attachment component (120a) and the second attachment component (120b).

8. The multi-purpose utility strap of claim 1, wherein the third attachment component (120c) is a first half hook-and-loop fastener and the fourth attachment component (120d) is a second half hook-and-loop fastener.

9. The multi-purpose utility strap of claim 1, wherein the third attachment component (120c) is a first half snap and the fourth attachment component (120d) is a second snap.

10. The multi-purpose utility strap of claim 1, wherein the third attachment component (120c) and the fourth attachment component (120d) comprise a hook mechanism, a button mechanism, a tie mechanism, a magnet mechanism, a snap mechanism, or a combination thereof.

11. The multi-purpose utility strap of claim 1, wherein the first attachment component (120a) can engage the fourth attachment component (120d).

12. The multi-purpose utility strap of claim 1, wherein the third attachment component (120c) can engage the second attachment component (120b).

13. The multi-purpose utility strap of claim 1, wherein the third attachment component (120c) can engage the first attachment component (120a).

14. The multi-purpose utility strap of claim 1, wherein the fourth attachment component (120d) can engage the second attachment component (120b).

15. A multi-purpose utility strap consisting of:
   (a) an elongated strap component (110) having a first end (111), a second end (112), a top surface (113), and a bottom surface (114);
   (b) a first attachment component (120a) disposed on the top surface (113) of the strap component (110) at the first end (111) and a second attachment component (120b) disposed on the top surface (113) of the strap component (110) near the first attachment component (120a), the first attachment component (120a) is adapted to engage the second attachment component (120b) to form a temporary loop at the first end (111) of the strap component (110); and
   (c) a third attachment component (120c) disposed on the bottom surface (114) of the strap component (110) at the second end (112) and a fourth attachment component (120d) disposed on the top surface (113) of the strap component (110) a distance from the second end (112), the third attachment component (120c) is adapted to engage the fourth attachment component (120d) to form a temporary loop at the second end (112) of the strap component (110); and (d) a first non-attaching region (131) disposed on the top surface (113) of the strap at the first end (111) between the first attachment component (120a) that is on the top surface (113) and the second attachment component (120b) that is on the top surface (113), a second non-attaching region (132) disposed on the top surface (113) of the strap between the second attachment component (120b) that is on the top surface (113) and the fourth attachment component (120d) that is on the top surface (113), and a third non-attaching region (133) disposed on the top surface (113) of the strap between the fourth attachment component (120d) that is on the top surface (113) and the third attachment component (120c) that is on the bottom surface (114) at the second end (112); wherein the first non-attaching region (131), the second non-attaching region (132), and the third non-attaching region (133) have only a strap component and no attachment components; wherein a length of the second non-attaching region (132) is longer than either a length of the first non-attaching region (131) or a length of the third non-attaching region (133), and wherein the length of the third non-attaching region is longer than the length of the first non-attaching region; and wherein the strap further comprises a fourth non-attaching region (134) disposed on the bottom surface (114) and is adjacent to the third attachment component (120c), and a length of the fourth non-attaching region (134) is longer than the length of the second non-attaching region (132); the fourth non-attaching region has only a strap component and no attachment component.

16. A multi-purpose utility strap comprising:

(a) an elongated strap component (110) having a first end (111), a second end (112), a top surface (113), and a bottom surface (114);

(b) a first attachment component (120a) disposed on the top surface (113) of the strap component (110) at the first end (111) and a second attachment component (120b) disposed on the top surface (113) of the strap component (110) near the first attachment component (120a), the first attachment component (120a) is adapted to engage the second attachment component (120b) to form a temporary loop at the first end (111) of the strap component (110); and (c) a third attachment component (120c) disposed on the bottom surface (114) of the strap component (110) at the second end (112) and a fourth attachment component (120d) disposed on the top surface (113) of the strap component (110) a distance from the second end (112), the third attachment component (120c) is adapted to engage the fourth attachment component (120d) to form a temporary loop at the second end (112) of the strap component (110); and (d) a first non-attaching region (131) disposed on the top surface (113) of the strap at the first end (111) between the first attachment component (120a) that is on the top surface (113) and the second attachment component (120b) that is on the top surface (113), a second non-attaching region (132) disposed on the top surface (113) of the strap between the second attachment component (120b) that is on the top surface (113) and the fourth attachment component (120d) that is on the top surface (113), and a third non-attaching region (133) disposed on the top surface (113) of the strap between the fourth attachment component (120d) that is on the top surface (113) and the third attachment component (120c) that is on the bottom surface (114) at the second end (112); wherein the first non-attaching region (131), the second non-attaching region (132), and the third non-attaching region (133) have only a strap component and no attachment components; wherein a length of the second non-attaching region (132) is longer than either a length of the first non-attaching region (131) or a length of the third non-attaching region (133), and wherein the length of the third non-attaching region is longer than the length of the first non-attaching region; and wherein the strap further comprises a fourth non-attaching region (134) disposed on the bottom surface (114), and a length of the fourth non-attaching region (134) is longer than the length of the second non-attaching region (132); the fourth non-attaching region has only a strap component and no attachment component.

* * * * *